United States Patent [19]

Sturm et al.

[11] 4,341,773

[45] Jul. 27, 1982

[54] 2,4-DIAMINO-5-SULFAMOYLBENZENE SULFONIC ACIDS AND PROCESS FOR THEIR MANUFACTURE

[75] Inventors: Karl Sturm, Heidesheim; Roman Muschaweck, Frankfurt am Main, both of Fed. Rep. of Germany

[73] Assignee: Hoechst Aktiengesellschaft, Frankfurt am Main, Fed. Rep. of Germany

[21] Appl. No.: 241,666

[22] Filed: Mar. 9, 1981

[30] Foreign Application Priority Data

Mar. 11, 1980 [DE] Fed. Rep. of Germany ....... 3009229

[51] Int. Cl.$^3$ .................. A61K 31/63; A61K 31/625; C07D 231/42; C07C 143/78
[52] U.S. Cl. .................................. 424/229; 424/228; 260/397.7 R; 260/239.6
[58] Field of Search .............................. 424/228, 229; 260/397.7, 239.6

[56] References Cited

U.S. PATENT DOCUMENTS

| 3,790,584 | 2/1974 | Feit et al. ..................... 260/397.7 R |
| 3,914,219 | 10/1975 | Lerch et al. ..................... 260/239.6 |
| 3,959,261 | 5/1976 | Lerch et al. ..................... 260/239.6 |
| 4,161,533 | 7/1979 | Sturm et al. ..................... 260/239.6 |

Primary Examiner—Alan Siegel
Attorney, Agent, or Firm—Curtis, Morris & Safford

[57] ABSTRACT

The present invention relates to compounds of the formula I

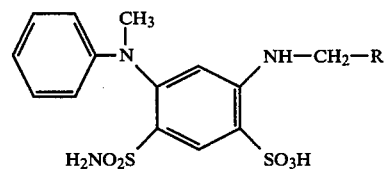

wherein R is furyl, thienyl or phenyl, to physiologically acceptable salts thereof, to a process for their manufacture, to a composition comprising said compounds and to their use as a medicament.

4 Claims, No Drawings

2,4-DIAMINO-5-SULFAMOYLBENZENE SULFONIC ACIDS AND PROCESS FOR THEIR MANUFACTURE

The present invention relates to compounds of the formula I

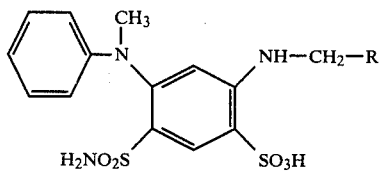

wherein R is furyl, thienyl or phenyl,
and to physiologically acceptable salts thereof. These compounds may be classified amongst the group of substituted 2,4-diamino-5-sulfamoylbenzene sulfonic acids.

R preferably stands for 2-furyl or 2-thienyl.

For the salt formation there may be used all physiologically acceptable cations, in particular the alkali metal or alkaline earth metal ions, the ammonium ion or substituted ammonium ions.

The present invention further relates to a process for the manufacture of the compounds of formula I, which comprises subjecting compounds of the formula II

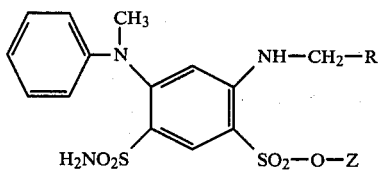

wherein Z is aryl, to an alkaline saponification and optionally converting the compound obtained into the free acid or a salt.

The radical Z in the starting compound of the formula II may in general be any aromatic radical, the phenyl or cresyl esters, that can be readily prepared, being particularly advantageous for an industrial-grade synthesis.

The alkaline saponification of the esters is preferably carried out in an aqueous medium using an inorganic base, in particular excess 1 N to 5 N sodium hydroxide solution or potassium hydroxide solution.

The starting compounds of formula II have not been before described in literature. For the preparation of these compounds there is suitably used as starting compound a 2,4-dichlorosulfamoylbenzene sulfonic acid ester of the formula III

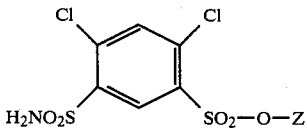

wherein Z preferably is phenyl or tolyl. The preparation of said esters is disclosed in German patent 2,718,871 (U.S. Pat. No. 4,161,533).

Said preparation of the starting compound of formula II comprises reacting in a first step a dichloro compound of formula III with N-methylaniline, at a temperature of from 120° to 140° C., using suitably an excess of a base, without addition of a solvent, and subsequently reacting the resulting N-methylaniline derivative of formula IV

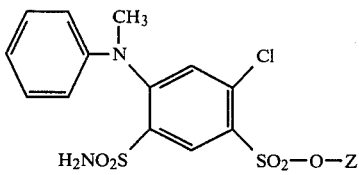

with an amine of the formula R—CH$_2$—NH$_2$, preferably used in an excess quantity, at a temperature of from 120° to 140° C. to obtain the desired compound of formula II.

For the alkaline saponification of the esters of formula II yielding the final products of formula I there are used preferably inorganic bases, more preferably aqueous sodium or potassium hydroxide solution. For example unsubstituted phenyl esters of formula II may be saponified with 2 N sodium or potassium hydroxide solution under reflux within 2 to 3 hours. Esters containing a phenol component of higher molecular weight may require the addition of an organic solvent miscible with water such as dioxan, glycol monomethyl ether or diglyme and/or a prolongation of the reaction time. Upon complete saponification the reaction solution is adjusted to a pH of from 7 to 8, preferably by adding dilute hydrochloric acid, whereupon the sodium or potassium salt of the final product precipitates in crystalline form already at room temperature.

When using an unsubstituted phenyl ester as the starting compound of formula II, the phenol obtained remains in the aqueous mother liquor and the product separated by suction-filtration is very pure after having been washed with water. If the phenol obtained upon saponification is less soluble in water, the crude product dried at the air is freed from the corresponding phenol by extraction with a suitable organic solvent such as diethyl ether, diisopropyl ether, toluene or ethyl acetate. A final purification takes place by recrystallizing the product from water or an alcohol-water mixture.

For therapeutic purposes there are preferably used the alkali metal salts, preferably the sodium or potassium salts of the compounds of the invention, these salts dissolving in water in satisfactory manner, with slightly alkaline reaction. The sodium salts having the best water-solubility are used above all for injection solutions, whereas the potassium salts having a lower water-solubility are particularly suitable for orally administrable galenic preparations.

Calcium, magnesium or ammonium salts of the compounds according to the invention may be used suitably for special therapeutic purposes. These salts are preferably precipitated in crystalline manner from an aqueous solution of the sodium salt by adding an excess of calcium chloride, magnesium chloride or of the corresponding amino hydrochloride amounting to several times the molecular quantity. They may likewise be obtained with the use of a ion exchanger, if they have a better water-solubility than the sodium salt.

The salt of the compounds according to the invention used in conjunction with basic, potassium-retaining compounds such as amiloride or triamters or with basic antihypertensive compounds such as clonidin, dihydralazine or β-blockers, are of particular pharmacological importance.

The compounds according to the invention are not very stable when present in the form of the free acid. If an administration in this form is intended, however, an aqueous solution of the sodium salt may be filtered by passing it over an acid ion exchanger followed by lyophilization of the filtered product.

The compounds according to the invention are excellent salidiuretics of the furosemide type. They are distinguished by an extremely strong action. As compared to known compounds of this type, they are moveover distinguished by a particularly low elimination of potassium and by a strong uricosuric action.

For therapy in man there are preferably used for oral adminstration tablets, dragees or capsules containing of from 0.1 to 50 mg of active substance.

The following examples serve to illustrate the invention

EXAMPLE 1:

Sodium salt of 2-furfurylamino-4-(N-methylanilino)-5-sulfamoylbenzene sulfonic acid 51.4 g of 2-furfurylamino-4-(N-methylanilino)-5-sulfamoylbenzene sulfonic acid phenyl ester (0.1 mol) are heated under reflux with 0.4 liter of 2 N NaOH for 3 hours. The reaction solution cooled to room temperature and filtered is adjusted to a pH of 7 with 2 N HCl, the crystalline precipitate obtained is left to stand for one hour at room temperature, subsequently suction-filtered and washed with a small quantity of ice water.

The slightly colored product still humid from the suction-filtration is recrystallized from water while using active carbon, and subsequently dried on a steam bath.

36 g of colorless prisms are obtained. Yield: 79% of the theory. Decomposition point: 195° C.

Starting material:

383 g of 2,4-dichloro-5-sulfamoylbenzene sulfonic acid phenyl ester (1.0 mol) are stirred with 500 ml of freshly distilled N-methylaniline under nitrogen at 130° C. for 8 hours. The reaction solution cooled to 50° C. is diluted with 0.4 liter of methanol and subsequently added, while stirring, into 5 liters of 2 N HCl. The amorphous precipitate obtained is decanted, recrystalized from 90% methanol, washed with ethanol and dried on a steam bath.

220 g of 2-chloro-4-(N-methylanilino)-5-sulfamoylbenzosulfonic acid phenyl ester of melting point 139°–141° C. are obtained. Yield: 49% of the theory.

182 g of said ester (0.4 mol) are stirred with 0.5 liter of freshly distilled furfurylamine for 2 hours at 125° C. and the reaction solution is added while stirring into 5 liters of 10% acetic acid. The crystalline precipitate obtained is suction-filtered, thoroughly washed with water and dried at the air.

190 g of 2-furfurylamino-4-(N-methylanilino)-5-sulfamoylbenzene sulfonic acid phenyl ester are obtained. Yield: 94% of the theory. The product sinters at a temperature above 80° C.

It is uniformous according to gas chromatographic analysis and can be used directly in the saponification.

EXAMPLE 2:

Sodium salt of 2-(2-thienylmethylamino)-4-(N-methylanilino)-5-sulfamoylbenzene sulfonic acid 53 g of 2-(2-thienylmethylamino)-4-(N-methylanilino)-5-sulfamoylbenzene sulfonic acid phenyl ester (0.1 mol) are refluxed for 3 hours with 0.5 liter of 2 N NaOH. The product obtained is cooled to room temperature whereupon 2 N HCl is added at pH 7 to precipitate the product in crystalline form. The crystals are washed subsequently with water and a small quantity of ethanol on a filter and dried at 100° C.

45 g of colorless crystals of a decomposition point of 215° C. are obtained. Yield: 95% of the theory.

Starting material:

182 g of 2-chloro-4-(N-methylanilino)-5-sulfamoylbenzene sulfonic acid phenyl ester (0.4 mol) are reacted with 0.5 liter of 2-thienylmethyl amine according to Example 1. Working up in the manner described in Example 1 gives 200 g of 2-(thienylmethylamino)-4-(N-methylanilino)-5-sulfamoylbenzene sulfonic acid phenyl ester in chromatographically pure form. Yield: 94% of the theory. The product sinters at a temperature above 90° C.

EXAMPLE 3:

Sodium salt of 2-benzylamino-4-(N-methylanilino)-5-sulfamoylbenzene sulfonic acid 52.4 g of 2-benzylamino-(N-methylanilino)-5-sulfamoylbenzene sulfonic acid phenyl ester (0.1 mol) are saponified with 2 N NaOH according to Example 2 and the final product is isolated in the manner described in said Example.

40 g of colorless crystals of a decomposition point of 245° C. are obtained. Yield: 80% of the theory.

Starting material:

2-Chloro-4-(N-methylanilino)-5-sulfamoylbenzene sulfonic acid phenyl ester is reacted with benzylamine in the manner described in Example 1.

What is claimed is:

1. Compounds of the formula I

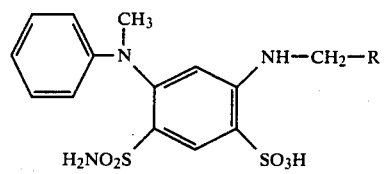

wherein R is furyl, thienyl or phenyl and physiologically acceptable salts thereof.

2. Compounds as claimed in claim 1, wherein R is 2-furyl or 2-thienyl.

3. A pharmaceutical composition which comprises an effective amount of a compound of the formula I as claimed in claim 1 as the active substance, in admixture or conjunction with a pharmaceutically suitable carrier and/or stabilizer.

4. Method of treatment which comprises administering a salidiuretically effective amount of a composition containing as the active substance a compound of the formula I as claimed in claim 1.

* * * * *